US00RE35823E

United States Patent [19]

Nabel et al.

[11] E Patent Number: Re. 35,823

[45] Reissued Date of Patent: Jun. 9, 1998

[54] PROTEINS USEFUL IN THE REGULATION OF κB-CONTAINING GENES

[75] Inventors: Gary J. Nabel; Roland M. Schmid; Neil D. Perkins, all of Ann Arbor, Mich.

[73] Assignee: The Regents of the University of Michigan, Ann Arbor, Mich.

[21] Appl. No.: 365,689

[22] Filed: Dec. 29, 1994

Related U.S. Patent Documents

Reissue of:

[64] Patent No.: 5,324,818
Issued: Jun. 28, 1994
Appl. No.: 747,781
Filed: Aug. 21, 1991

[51] Int. Cl.[6] ..... C07K 14/00

[52] U.S. Cl. ..... 530/350; 435/172.3; 935/11; 935/34; 935/36

[58] Field of Search ..... 530/350; 435/172.3; 935/34, 36, 11

[56] References Cited

PUBLICATIONS

Ansorge et al., Nucleic Acids Res., vol. 15, pp. 4593–4602, 1987.
Brumbaugh et al., PNAS, vol. 85, pp. 5610–5614, 1988.
Cathcart et al., Nature, vol. 347, p. 310, 1990.
Connell et al., Biotechniques, vol. 5, pp. 342–344, 1987.
Lee et al., Nucleic Acids Res., vol. 20, pp. 2471–2483, 1992.
Prober et al., Science, vol. 238, pp. 336–341, 1987.
Sanger et al., PNAS, vol. 74, pp. 5463–5467, 1977.
Smith et al., Nucleic Acids Res., vol. 13, pp. 2399–2412, 1985.
Smith et al., Nature, vol. 321, pp. 674–679, 1986.
Franza et al., Nature vol. 330, pp. 391–395 (1987).
Ghash et al., Cell vol. 62, pp. 1019–1029 (1990).
Publication—"Tampering with Transcription", by Gary J. Nabel, News and Views, Nature, vol. 350, Apr. 25, 1991, p. 658.
Aids Research Reviews, vol. 1, Chapter 2, by Gary J. Nable, Marcel Dekker, Inc., New York, Basel, Hong Kong, pp. 21–34, Chapter 2 entitled "Cellular Regulation of Human Immunodeficiency Virus Gene Expression".
Helene et al., *Biochimica et Biophysica Acta.*, vol. 1049, pp. 99–145 (1990).

*Primary Examiner*—David Guzo

[57] ABSTRACT

Proteins, and corresponding DNA and RNA sequences, useful for the regulation of expression of κB-containing genes are disclosed. These proteins are useful to either stimulate or inhibit the expression of κB-containing genes. Proteins stimulating the expression of κB-containing genes have an amino acid sequence at least 80% identical to the amino acid sequence of from position 1 to position 374 of p100 [SEQ ID NO: 2]. Proteins having an inhibitory effect on the expression of κB-containing genes have sequences either at least 80% identical to the amino acid sequence of from position 407 to the carboxyl end of p100 [SEQ ID NO: 2] or having an amino acid sequence at least 80% identical to the amino sequence of either from position 1 to 100 sor from position 101 to position 374 of p100 [SEQ ID NO: 2].

2 Claims, 1 Drawing Sheet

PROTEINS USEFUL IN THE REGULATION OF κB-CONTAINING GENES

Matter enclosed in heavy brackets [ ] appears in the original patent but forms no part of this reissue specification; matter printed in italics indicates the additions made by reissue.

The technology described in this document is in part based on work funded by the National Institute of Health (Grant Nos. AI26864 and AI29179).

BACKGROUND OF THE INVENTION

1. Field of the Invention

The present invention relates to genetic sequences and proteins useful in the regulation of genes, particularly in the regulation of κB-containing genes.

2. Discussion of the Background

A twice-repeated 11-base-pair sequence, termed κB, which is known to exist in association with the enhancer of the immunoglobulin κ light chain (Sen et al, Cell (1986) 46:705, Sen et al, Cell (1986) 47:729) is present in the control elements of numerous genes, including both vital and cellular genes. NF-κB, a regulatory element originally described as a transcription factor that recognizes the κB element of the immunoglobulin (Ig) κ light chain enhancer and which is known to be associated with κ light chain expression, has been found in a variety of vital enhancers, including SV40, CMV, HIV-2 and SIV. κB-related sites have been found in association with several cellular genes, including class I and II MHC genes, IL-2, IL-2 receptor (IL-2Rα), serum amyloid A, β-2 micro-globulin, β-interferon, tumor necrosis factor, and T-cell receptor genes.

A κB-like site contributes functionally to IL-2-dependent gene expression and may also regulate IL-2Rα transcription. κB is also found among the regulatory elements upstream of the HIV enhancer. This site was initially identified as a positive regulatory element recognized by DNA binding proteins found to be present in activated, but not resting, T cells. Mutation of the κB sites abolished inducibility of the HIV enhancer in T leukemia cells. A link between the κB site and the tat-I gene was also suggested by the synergistic response of the HIV enhancer to tat-I and NF-κB-mediated stimulation.

Another κB-like site was found upstream of the class I MHC gene. Although this site competes for binding to NF-κB, a DNA binding protein distinct from NF-κB has been identified in MEL and HeLa cells. Baldwin et al, Proc. Nat. Acad. Sci. (USA) (1988) 85:723. This protein, termed H2TF1, was detected in nuclear extracts containing no detectable NF-κB binding activity and had a different apparent molecular weight as measured by UV-cross-linking analysis. Another protein, designated KBF1, also recognized this site and may be related in part to NF-κB. Israel et al, Proc. Nat. Acad. Sci. (USA) (1987) 84:2653, Yanno et al, EMBO J (1987) 6:3317.

Although these proteins recognize κB-like sites, their relationship to the IL-2R κB binding protein(s) and NF-κB is unknown. Similarly, the HIVen86 protein is likely to be distinct from NF-κB since it has a higher apparent molecular weight. Franza et al, Nature (1987) 330:391. Its relationship to the IL-2R κB binding protein, which has been designated RκB (NF-rκB), and its role in mediating transactivation dependent on these κB-like sites is also not yet understood. Although the evidence is indirect, it appears that HIVen86 also differs from RκB, which has a higher apparent molecular weight of 100 kD.

While extensive sequence similarity to κB is found among enhancers associated with several genes (Lung et al, Nature (1988) 333:776), a second characteristic shared by these sites is their ability to respond to transactivation by the $tax_1$ gene of HTLV-1. At the same time, several lines of evidence suggest differences among κB binding proteins. For example, nuclear extracts from MEL cells display an H2TF1 binding activity in the absence of detectable NF-κB binding. Competition studies showed that both the IL-2RκB and κB sites compete less efficiently than H2TF1 for binding to the site, consistent with previous studies suggesting that a distinct binding protein binds to the H2TF1 site.

Analysis of binding proteins by UV-cross-linking and SDS-page has also revealed multiple radiolabeled complexes, further implicating multiple proteins in κB binding. By UV-cross-linking, several specific complexes have been detected, including proteins of molecular weights of ca. 160, ca. 90, ca. 75, and ca. 50 kD. There is no evidence for differential regulation of these proteins by different NF-κB stimulants since PMA, TNF-α, and IL-1 induce the same set of complexes. The complex of ca. 50 kD is consistent with previous report of NF-κB and/or κBF1. Although a κB binding protein of 86 kD HIVen86A, has also been identified by two-dimensional gel electrophoresis, it is unclear whether the ca. 90 kD protein represents this protein. Both HIVen86 and RκB show no increase in binding following cellular activation. The 160 kD complex has not been previously described.

In summary, at least seven κB binding proteins have been defined to date by either mobility shift analysis, UV-crosslinking, or protein purification. The molecular weight of these proteins range in size from 48 to greater than 300 kD. The various κB binding proteins that have been reported are indicated in Table 1 below, together with their relative specificities for the canonical κB, the class I MHC, and the IL-2RκB sites.

TABLE 1

Summary of κB Binding Proteins

| Name | Specificity | Protein (kD) | cDNA (kb) |
|---|---|---|---|
| NF-κB/KBFI | κB = MHC = IL-2RκB | 50 | 4 |
| H2TF-1 | MHC > κB > IL-2RκB | 110 | — |
| EBP-1 | MHC = κB | 60 | — |
| HIVen86 | κB = IL-2RκB | 86 | — |
| MBP-1 | MHC > κB > IL-2RκB | ~300 | 9.5 |
| RκB (IL-2RκB) | IL-2RκB > κB > MHC | 95 | 5.5 |

Of these, the cDNAs encoding three of these proteins have been isolated. These cDNAs differ from one another by primary sequence and react with mRNAs of distinct size by northern blot. Taken together, these data indicate that multiple proteins could bind to a set of κB-related sites. Thus, there is a family of κB binding proteins, which, unlike some DNA binding proteins (e.g., c-jun), do not appear to be members of a related multigene family.

The κB sequence is known to exist in association with the regulatory elements of various viral and cellular genes. In light of the obvious interest in regulating gene expression there is accordingly a need for a factor useful in the regulation of κB-containing genes.

SUMMARY OF THE INVENTION

Accordingly, it is an object of this invention to provide novel factors, and materials and methods useful for obtaining and using such factors, useful in the regulation of κB-containing genes.

The above objects, of the invention, and other objects which will become apparent from the description of the invention given hereinbelow, have been surprisingly found to be satisfied by proteins having amino acid sequences related to p49 [SEQ ID NO: 1] and p100 [SEQ ID NO: 1]. More particularly, the inventors have discovered that proteins having amino acid sequences at least 80%, preferably at least 90% and more preferably at least 95%, identical to either (i) the sequence of from amino acid position about 1 to amino acid position about 374 and up to the complete sequence of p49 [SEQ ID NO: 1] or (ii) the sequence of from amino acid position about 1 to amino acid position about 374 and up to amino acid position about 500 of p100 [SEQ ID NO: 2] are useful to stimulate the expression of κB-containing genes. The inventors have also discovered related proteins useful in inhibiting the expression of κB-containing genes. These proteins may be characterized by amino acid sequences at least 80%, preferably at least 90% and more preferably at least 95%, identical to the sequence of from amino acid position about 407 of p100 [SEQ ID NO: 2]. The proteins exhibiting the inhibitory effect may also be characterized by amino acid sequences at least 80%, preferably at least 90% and more preferably at least 95%, identical to the sequence of from either (i) amino acid positions about 1 to about 190 or (ii) positions about 191 to about 374 of p100 [SEQ ID NO: 2] and up to about complete p100 [SEQ ID NO: 2].

BRIEF DESCRIPTION OF THE FIGURES

The figures set forth the deduced amino acid sequence of the p49 [SEQ ID NO: 1] and p100 [SEQ ID NO: 2] NF-κB proteins—two proteins provided by the invention—and their similarity to other NF-κB/rel/dorsal gens. More particularly, FIG. 1 provides a schematic comparison of the major structural features of p49 [SEQ ID NO: 1] and p100 [SEQ ID NO: 2]. [FIG. 2 provides the deduced amino acid sequence of p49 [SEQ ID NO: 1] and p100 [SEQ ID NO: 2] and comparison to p105 NF-κB [SEQ ID NO: 3].]

DETAILED DESCRIPTION OF THE PREFERRED EMBODIMENTS

Figure 1:
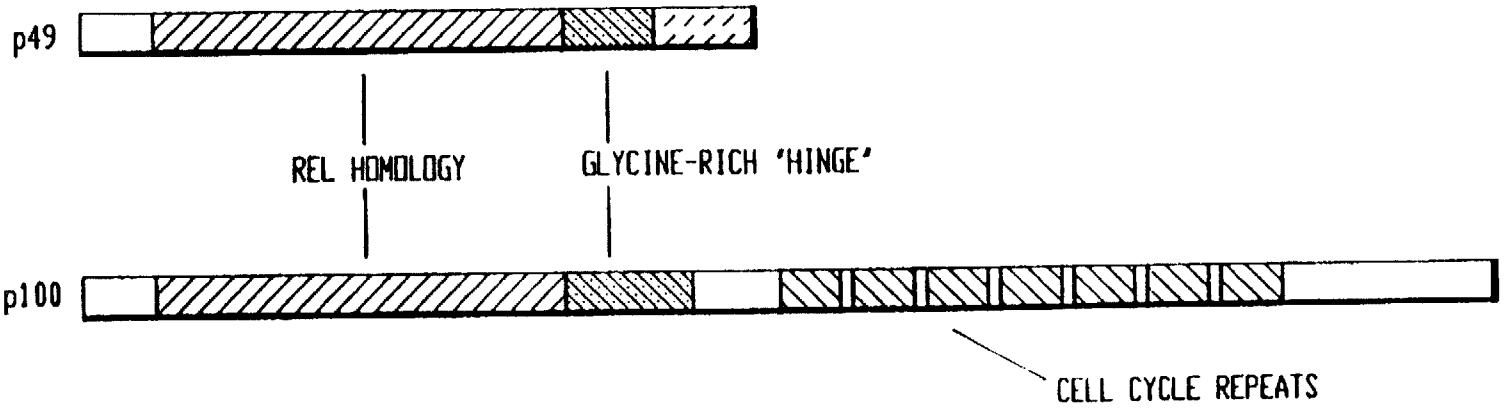

The transcription factor NF-κB is a protein complex which comprises a DNA-binding subunit and an associated transactivation protein (of relative molecular masses 50,000 (50K) and 65K, respectively). Both the 50K and 65K subunits have similarity with the rel oncogene and the Drosophila maternal effect gene dorsal. The 50K DNA-binding subunit was previously thought to be a unique protein, derived from the 105K gene product (p105). The present invention is based on the inventor's discovery of a complementary DNA (cDNA) that encodes an alternative DNA-binding subunit of NF-κB. This cDNA is more similar to p105 NF-κB than other family members and defines a new subset of rel-related genes.

It is synthesized as a ca.100K protein (p100) that is expressed in different cell types, contains cell cycle motifs and, like p105, must be processed to generate a 50K form. A 49K product (p49) can be generated independently from an alternatively spliced transcript; it has specific κB DNA-binding activity and can form heterodimers with other rel proteins. In contrast to the ca.50K protein derived from p105, p49 acts in synergy with p65 to stimulate the human immunodeficiency virus (HIV) enhancer in transiently transfected Jurkat cells. The p49/p100 NF-κB is therefore important in the regulation of κB-contalning genes, including HIV.

The present invention accordingly provides proteins useful in the regulation of κB-containing genes. These proteins may be used to either stimulate or inhibit the expression of κB-containing genes. These proteins are based on the inventor's discovery that the amino acid sequence located at positions about 1 to about 374 of p49 [SEQ ID NO: 1] and up to the complete sequence of p49 [SEQ ID NO: 1], simulates the expression of κB-containing genes. (Note that p49 [SEQ ID NO: 1] and p100 [SEQ ID NO: 2] are identical from positions 1 to 374.) The inventor has further discovered that the amino acid sequence found at about positions about 1 to about 190 of p100 [SEQ ID NO: 2] is a DNA binding domain and that the amino acid sequence found at positions about 191 to about 374 of p100 [SEQ ID NO: 2] is a dimerization interface. And the inventor has still further discovered that the amino acid sequence found at position about 407 of p100 [SEQ ID NO: 2] going all the way to about the carboxyl terminal of the protein is also capable of inhibiting the expression of κB-containing genes.

The proteins provided by the present invention which accordingly act to stimulate κB-containing genes have in amino acid sequence at least 80% identical (i.e. up to 20% of the amino acids have been changed, deleted, or both), preferably 90% identical, and most preferably 95% identical, to the amino acid sequence of amino acid positions about 1 to about 374 of either p49 [SEQ ID NO: 1] or p100 [SEQ ID NO: 2] and optionally up to about the complete sequence of p49 [SEQ ID NO: 1] or up to amino acid position about 500 of p100 [SEQ ID NO: 2].

Proteins useful in inhibiting κB-containing genes provided by the invention are of two related types. The first is a transdominant mutant of p49 [SEQ ID NO: 1] in which either (i) the dimerization interface region of p49 [SEQ ID NO: 1] has been retained (located at positions about 191 to about 374 of p100 [SEQ ID NO: 2]) or (ii) the DNA binding region (located in positions about 1 to about 190 of p100 [SEQ ID NO: 2]) has been retained. In either of these two embodiments the other (i.e. unretained) region has been either removed or altered to cause loss of DNA binding or of dimerization activity, e.g., by removing or replacing at least 10 % of its amino acids, preferably at least 25% of its amino acids, to achieve removal of DNA binding or dimerization activity.

This transdominant mutant of p49 [SEQ ID NO: 2] may be a protein having in amino acid sequence at least 80% identical, preferably 90% identical, and most preferably 95% identical, to either (i) the amino acid sequence of amino acid positions about 1 to about 190 or (ii) the amino acid sequence of amino acid positions about 191 to about 374 of either p49 or p100 [SEQ ID NO: 1 or 2] and optionally up to the complete p49 [SEQ ID NO: 1] or complete p100 [SEQ ID NO: 2]. That is, if the protein is one in which the DNA binding region has been altered or removed, the protein may further comprise, attached to its carboxyl end, an amino acid sequence at least 80% identical, preferably 90% identical, and more preferably 95% identical to up to 100%, the amino acid sequence of from positions 374 to the carboxyl end of p100 [SEQ ID NO: 2].

With the above transdominant mutant of p49 [SEQ ID NO: 1] one uses either the protein segment comprising the DNA binding region or the protein segment comprising the dimerization interface region of p49 [SEQ ID NO: 1]. The DNA binding region may be used by itself or it may be used in association with an inactivated dimerization interface, where the inactivation results from removal of at least 10%, or preferably 25% amino acids from the dimerization interface region. If a protein segment corresponding to the dimerization interface region is used, it may be used by itself or in association with an inactivated DNA binding region.

where inactivation is caused by the removal of at least 10%, preferably at least 25% of the amino acids from the DNA binding region.

Another group of κB inhibiting proteins provided by the present invention have an amino acid sequence at least 80% identical, preferably 90% identical, and most preferably 95% identical to the sequence of ammo acid at positions about 407 of p100 [SEQ ID NO: 2] to about the carboxy end of p100 [SEQ ID NO: 2].

The present invention also provides DNA and RNA sequences encoding to the above proteins, corresponding antisense RNA sequences, vectors useful to express these proteins, and both eukaryotic and prokaryotic cells containing these DNA and/or RNA sequences, further optionally containing a κB-containing gene.

The antisense RNA sequences provided by the present invention may be one of five different types. The first is an antisense RNA sequence which is at least 20 nucleotides-long and corresponds to an amino acid sequence falling within positions 1 to 374 of p49 [SEQ ID NO: 1], inclusive. The second is an antisense RNA sequence which is at least 20 nucleotides-long and corresponds to an amino acid sequence falling within the sequence of p49 [SEQ ID NO: 1]. The third is an antisense RNA sequence which is at least 20 nucleotides-long and corresponds to an amino acid sequence falling within the sequence of p100 [SEQ ID NO: 2]. The fourth is an antisense RNA sequence which is at least 20 nucleotides-long which corresponds to an amino acid sequence falling within the sequence of from position 375 to the carboxyl end of p49 [SEQ ID NO: 1], inclusive. The fifth is an antisense RNA sequence which is at least 20 nucleotides-long and corresponds to an amino acid sequence falling within positions 375 to the carboxyl end of p100 [SEQ ID NO: 2], inclusive.

These antisense RNA sequences may be used in accordance with known techniques (see, e.g., Zamecnik et al, Proc. Nat. Acad. Sci. (USA), (1986) 83:4143–4146) to inhibit or block cellular expression of the genes encoding either p49 [SEQ ID NO: 1] or p100 [SEQ ID NO: 2]. More particularly the above first, second and third antisense RNA sequences may be used to inhibit or block expression of either p49 [SEQ ID NO: 1] or p100 [SEQ ID NO: 2]. The fourth antisense RNA sequence may be used to inhibit or block expression of p49 [SEQ ID NO: 1] because it is drawn to a sequence unique to p49 [SEQ ID NO: 1]. The above fifth antisense RNA sequence may be used to inhibit or block expression of p100 [SEQ ID NO: 2] because it is drawn to a sequence unique to p100 [SEQ ID NO: 2].

The eukaryotic and prokaryotic cells provided by the present invention contain the DNA and/or RNA sequences encoding a present protein, optionally together with a κB-containing gene. These latter sequences (i.e., the sequences containing the κB sites) are present in these cells in a geometry permitting regulation of the κB-containing gene by the proteins of the present invention.

The p49/p100 subunit of NF-κB provided by the invention can be used to regulate the expression of recombinant genes in eukaryotic or prokaryotic cells. In one form of this method, the p49/p100 gene can be overexpressed in a host cell which contains a separate κB-dependent enhancer to express a given recombinant gene. When the p49 gene is overexpressed, the κB-regulated enhancer will stimulate expression of the recombinant gene of interest.

In another method, it is possible to use the κB site to block transcriptional activation. By placing the κB binding sites within a promoter near the transcriptional initiation site, it would interfere with transcriptional initiation or elongation when the recombinant p49/p100 proteins could bind to these sites. It is therefore possible to inhibit expression of a specific recombinant gene when this molecule is overexpressed.

Another way to regulate expression of recombinant genes within cells is to make a fusion protein between p49 (or p100) gene products, for example, the DNA binding and dimerization domains and fuse them to an acidic transactivation domain, such as that of the herpesvirus transactivator, VP16. Such chimeric constructs would provide a high level of constitutive transactivation to κB-dependent plasmids.

Several such plasmids can be synthesized whereby fusion proteins have been linked to the 3'-end of either p49 or an equivalent of p100, creating potent transactivators. Such chimeric transactivators can also be used to overexpress recombinant proteins with cells.

The NF-κB-related DNA and RNA or protein sequences provided by the inventors can be utilized for a variety of different functions. First, the recombinant protein can be used to generate antibodies against this gene product to detect this protein within cells or tissues. Since these proteins are involved in the regulation of HIV and may also be related to cell division and malignancy, this would provide a useful assay to determine the degree of progression of HIV or the degree of activation of malignant cells.

In addition, the DNA or RNA sequences can be measured directly following HIV infection as an indicator of the activity of virus within cells. In recent studies, the inventors have noted a decrease in p100 expression following HIV infection in cell culture. The recombinant proteins can also be used to generate transdominant mutants which can be used to inhibit activation of HIV, normal cellular genes, or cell replication. The purified recombinant proteins may also be used to define mechanisms of transcriptional activation in the laboratory to determine the specificity of DNA binding, and to determine the 3-dimensional structure of these proteins for further attempts at molecular modeling and rational drug design.

Cultures of E. coli XL-blue cells transformed with bluescript plasmids containing p49 [SEQ ID NO: 1] or p100 [SEQ ID NO: 2] encoding inserts have been deposited in the permanent culture collection of the American Type Culture Colection (ATCC), located at 12301 Parklawn Drive, Rockville, Md. 20852 USA, on Aug. 20, 1991. These cultures have been accorded the following accession numbers: 68672 and 68673.

Having generally described this invention, a further understanding can be obtained by reference to certain specific examples which are provided herein for purposes of illustration only and are not intended to be limiting unless otherwise specified.

Experimental

To characterize the molecular structure of NF-κB and its mechanism of activation, the inventor attempted to identify cDNAs that encode proteins within this complex. Trypsin digested κB binding proteins purified from bovine spleen were sequenced. Three peptides so obtained were identical to a DNA binding subunit of human NF-κB/κBF1, while another was 75% identical to a homologous peptide of p105. This peptide sequence suggested the existence of an alternative NF-κB protein. A PCR probe amplified from degenerate primers was found to be identical to a 700 bp fragment of human c-rel and was used for low stringency hybridization.

From $6\times10^5$ recombinants, two clones were identified which hybridized at low stringency. By Southern blot analysis at high stringency, this gene was present in single copy, and Northern blot analysis revealed at least two hybridizable RNA species of ~1.9 kb and ~3.5 kb, demonstrating that multiple species of p49 existed, and their relative abundance varied among different cell types. For example, the larger 3.5 kb species, found in all cells examined, was the predominant form in YT T leukemia cells; but both transcripts were present equally in the JY B cell line.

To characterize the larger mRNA species, additional cDNA clones were isolated and sequenced. The clone for the shorter transcript contained a 1341 bp open reading frame, predicting a protein of MW ~49,100. The longer clone encoded a protein of predicted MW, ~100,634 kd. These sequences were identical through amino acid 374, into the glycine-rich putative hinge region, after which they diverged. The amino acid sequence in the common N-terminal region was similar (26% identity) to NF-κB, dorsal and rel, with greatest similarity between p49/p100 and p105 (60% identity). One subregion contained conserved cysteine and histidine residues that do not form a classic zinc finger structure. Interestingly, κB-binding activity is dependent upon zinc, and, analogous to the tat-I gene of HIV, may form an alternative structure which participates in dimerization or nucleic acid binding. The longer transcript contained repeated sequences in the C-terminal region with homology to motifs in p105 and cell cycle genes. Among these family members, p100 NF-κB is most closely related to p105 NF-κB (41% identity), while p65 is most similar to c-rel (50% identity).

To characterize the DNA binding activity of the p49 cDNA, the electrophoretic mobility shift assay (EMSA) was performed using a prokaryotic expression system. The predominant product of ~49 kd displayed specific κB binding activity which was competed by the H-2 and HIV κB sites, but not by a single base pair mutant of HIV or an unrelated IL-2 octamer site. Interaction of p49 with other rel family members was examined by immunoprecipitation in a wheat germ co-translation system similar to p105(Xba I), p49 associated with c-rel.

To determine whether p49 interacts with other NF-κB/rel proteins to stimulate transcription, eukaryotic expression vectors were transfected into Jurkat cells. Transfection of p49 alone stimulated κB enhancer activity slightly, while p65 at higher concentrations significantly increased κB-dependent transcription. Transfection of low amounts (≦1 μg) of either p49 or p65 caused minimal stimulation, but when co-transfected together, they acted in synergy to stimulate a κB reporter plasmid. This stimulation was more effective than the combination of "p50" [p105(Rsa I)] and p65, suggesting that p49 was more effective in cooperating with p65. When analyzed with the HIV-CAT reporter, the p49/p65 combination, but not p50 [p105(Rsa I)]/p65, stimulated HIV-CAT activity, and the effect required an intact κB regulatory element. A truncated p100 (48.5 kd form) showed similar stimulation, in contrast to full-length p100 which was inactive, suggesting that differences in the rel-conserved domain mediate this effect.

These findings demonstrate that κB-dependent transcription is regulated by the p49/100 gene products. p65 and tel are putative transcriptional activation subunits with intrinsic DNA binding activity which associate with another DNA binding subunit, previously thought to be a single gene product derived from p105. These findings suggest that p49/100 represents an alternative DNA binding subunit of NF-κB which synergizes effectively with p65 to activate κB-dependent transcription. Many proteins can bind to κB-related sites, some of which are not NF-κB/rel-related. Although a variety of κB-binding proteins have been defined biochemically, their identification has remained equivocal since related antigenic epitopes are contained in their amino terminal region. As with p49/100, the identification of these cDNAs allows more definitive analysis of their expression and function. The interaction of p49/100 with other proteins and its potential alternative modes of regulation may provide additional mechanisms to regulate the transcription of HIV and different κB-containing genes.

Obviously, numerous modifications and variations of the present invention are possible in light of the above teachings. It is therefore to be understood that within the scope of the appended claims, the invention may be practiced otherwise than as specifically described herein.

---

*SEQUENCE LISTING*

*( 1 ) GENERAL INFORMATION:*

*( i i i ) NUMBER OF SEQUENCES: 3*

*( 2 ) INFORMATION FOR SEQ ID NO:1:*

*( i ) SEQUENCE CHARACTERISTICS:*
*( A ) LENGTH: 447 amino acids*
*( B ) TYPE: amino acid*
*( D ) TOPOLOGY: unknown*

*( i i ) MOLECULE TYPE: protein*

*( x i ) SEQUENCE DESCRIPTION: SEQ ID NO:1:*

```
Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45
```

-continued

Arg Gly Phe Arg Phe Arg Tyr Gly Cys Glu Gly Pro Ser His Gly Gly
50 55 60

Leu Pro Gly Ala Ser Ser Glu Lys Gly Arg Lys Thr Tyr Pro Thr Val
65 70 75 80

Lys Ile Cys Asn Tyr Glu Gly Pro Ala Lys Ile Glu Val Asp Leu Val
85 90 95

Thr His Ser Asp Pro Pro Arg Ala His Ala His Ser Leu Val Gly Lys
100 105 110

Gln Cys Ser Glu Leu Gly Ile Cys Ala Val Ser Val Gly Pro Lys Asp
115 120 125

Met Thr Ala Gln Phe Asn Asn Leu Gly Val Leu His Val Thr Lys Lys
130 135 140

Asn Met Met Gly Thr Met Ile Gln Lys Leu Gln Arg Gln Arg Leu Arg
145 150 155 160

Ser Arg Pro Gln Gly Leu Thr Glu Ala Glu Gln Arg Glu Leu Glu Gln
165 170 175

Glu Ala Lys Glu Leu Lys Lys Val Met Asp Leu Ser Ile Val Arg Leu
180 185 190

Arg Phe Ser Ala Phe Leu Arg Ala Ser Asp Gly Ser Phe Ser Leu Pro
195 200 205

Leu Lys Pro Val Thr Ser Gln Pro Ile His Asp Ser Lys Ser Pro Gly
210 215 220

Ala Ser Asn Leu Lys Ile Ser Arg Met Asp Lys Thr Ala Gly Ser Val
225 230 235 240

Arg Gly Gly Asp Glu Val Tyr Leu Leu Cys Asp Lys Val Gln Lys Asp
245 250 255

Asp Ile Glu Val Arg Phe Tyr Glu Asp Asp Glu Asn Gly Trp Gln Ala
260 265 270

Phe Gly Asp Phe Ser Pro Thr Asp Val His Lys Gln Tyr Ala Ile Val
275 280 285

Phe Arg Thr Pro Pro Tyr His Lys Met Lys Ile Glu Arg Pro Val Thr
290 295 300

Val Phe Leu Gln Leu Lys Arg Lys Arg Gly Gly Asp Val Ser Asp Ser
305 310 315 320

Lys Gln Phe Thr Tyr Tyr Pro Leu Val Glu Asp Lys Glu Glu Val Gln
325 330 335

Arg Lys Arg Arg Lys Ala Leu Pro Thr Phe Ser Gln Pro Phe Gly Gly
340 345 350

Gly Ser His Met Gly Gly Gly Ser Gly Gly Ala Ala Gly Gly Tyr Gly
355 360 365

Gly Ala Gly Gly Gly Glu Gly Val Leu Met Glu Gly Gly Val Lys Val
370 375 380

Arg Glu Ala Val Glu Glu Lys Asn Leu Gly Glu Ala Gly Arg Gly Leu
385 390 395 400

His Ala Cys Asn Pro Ala Phe Gly Arg Pro Arg Gln Ala Asp Tyr Leu
405 410 415

Arg Ser Gly Val Gln Asp Gln Leu Gly Gln Gln Arg Glu Thr Ser Ser
420 425 430

Leu Leu Lys Ile Gln Thr Leu Ala Gly His Gly Gly Arg Arg Leu
435 440 445

( 2 ) INFORMATION FOR SEQ ID NO:2:

( i ) SEQUENCE CHARACTERISTICS:

-continued (A) LENGTH: 899 amino acids
(B) TYPE: amino acid
(D) TOPOLOGY: unknown (ii) MOLECULE TYPE: protein (xi) SEQUENCE DESCRIPTION: SEQ ID NO:2:

```
Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp
        115                 120                 125

Met Thr Ala Gln Phe Asn Asn Leu Gly Val Leu His Val Thr Lys Lys
    130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Thr Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
    290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350

Gly Ser His Met Gly Gly Gly Ser Gly Gly Ala Ala Gly Gly Tyr Gly
        355                 360                 365

Gly Ala Gly Gly Gly Gly Ser Leu Gly Phe Phe Pro Ser Ser Leu Ala
    370                 375                 380
```

-continued

Tyr Ser Pro Tyr Gln Ser Gly Ala Gly Pro Met Gly Cys Tyr Pro Gly
385 390 395 400

Gly Gly Gly Gly Ala Gln Met Ala Ala Thr Val Pro Ser Arg Asp Ser
405 410 415

Gly Glu Glu Ala Ala Glu Pro Ser Ala Pro Ser Arg Thr Pro Gln Cys
420 425 430

Glu Pro Gln Ala Pro Glu Met Leu Gln Arg Ala Arg Glu Tyr Asn Ala
435 440 445

Arg Leu Phe Gly Leu Ala Gln Arg Ser Ala Arg Ala Leu Leu Asp Tyr
450 455 460

Gly Val Thr Ala Asp Ala Arg Ala Leu Leu Ala Gly Gln Arg His Leu
465 470 475 480

Leu Thr Ala Gln Asp Glu Asn Gly Asp Thr Pro Leu His Leu Ala Ile
485 490 495

Ile His Gly Gln Thr Ser Val Ile Glu Gln Ile Val Tyr Val Ile His
500 505 510

His Ala Gln Asp Leu Gly Val Val Asn Leu Thr Asn His Leu His Gln
515 520 525

Thr Pro Leu His Leu Ala Val Ile Thr Gly Gln Thr Ser Val Val Ser
530 535 540

Phe Leu Leu Arg Val Gly Ala Asp Pro Ala Leu Leu Asp Arg His Gly
545 550 555 560

Asp Ser Ala Met His Leu Ala Leu Arg Ala Gly Ala Gly Ala Pro Glu
565 570 575

Leu Leu Arg Ala Leu Leu Gln Ser Gly Ala Pro Ala Val Pro Gln Leu
580 585 590

Leu His Met Pro Asp Phe Glu Gly Leu Tyr Pro Val His Leu Ala Val
595 600 605

Arg Ala Arg Ser Pro Glu Cys Leu Asp Leu Leu Val Asp Ser Gly Ala
610 615 620

Glu Val Glu Ala Thr Glu Arg Gln Gly Gly Arg Thr Ala Leu His Leu
625 630 635 640

Ala Thr Glu Met Glu Glu Leu Gly Leu Val Thr His Leu Val Thr Lys
645 650 655

Leu Arg Ala Asn Val Asn Ala Arg Thr Phe Ala Gly Asn Thr Pro Leu
660 665 670

His Leu Ala Ala Gly Leu Gly Tyr Pro Thr Leu Thr Arg Leu Leu Leu
675 680 685

Lys Ala Gly Ala Asp Ile His Ala Glu Asn Glu Glu Pro Leu Cys Pro
690 695 700

Leu Pro Ser Pro Pro Thr Ser Asp Ser Asp Ser Asp Ser Glu Gly Pro
705 710 715 720

Glu Lys Asp Thr Arg Ser Ser Phe Arg Gly His Thr Pro Leu Asp Leu
725 730 735

Thr Cys Ser Thr Lys Val Lys Thr Leu Leu Leu Asn Ala Ala Gln Asn
740 745 750

Thr Met Glu Pro Pro Leu Thr Pro Pro Ser Pro Ala Gly Pro Gly Leu
755 760 765

Ser Leu Gly Asp Thr Ala Leu Gln Asn Leu Glu Gln Leu Leu Asp Gly
770 775 780

Pro Glu Ala Gln Gly Ser Trp Ala Glu Leu Ala Glu Arg Leu Gly Leu
785 790 795 800

Arg Ser Leu Val Asp Thr Tyr Arg Gln Thr Thr Ser Pro Ser Gly Ser
805 810 815

Leu Leu Arg Ser Tyr Glu Leu Ala Gly Gly Asp Leu Ala Gly Leu Leu
820 825 830

Glu Ala Leu Ser Asp Met Gly Leu Glu Glu Gly Val Arg Leu Leu Arg
835 840 845

Gly Pro Glu Thr Arg Asp Lys Leu Pro Ser Thr Glu Val Lys Glu Asp
850 855 860

Ser Ala Tyr Gly Ser Gln Ser Val Glu Gln Glu Ala Glu Lys Leu Gly
865 870 875 880

Pro Pro Pro Glu Pro Pro Gly Gly Leu Cys His Gly His Pro Gln Pro
885 890 895

Gln Val His ( 2 ) INFORMATION FOR SEQ ID NO:3:

( i ) SEQUENCE CHARACTERISTICS:
( A ) LENGTH: 969 amino acids
( B ) TYPE: amino acid
( D ) TOPOLOGY: unknown ( i i ) MOLECULE TYPE: protein ( x i ) SEQUENCE DESCRIPTION: SEQ ID NO:3:

Met Ala Glu Asp Asp Pro Tyr Leu Gly Arg Pro Glu Gln Met Phe His
1 5 10 15

Leu Asp Pro Ser Leu Thr His Thr Ile Phe Asn Pro Glu Val Phe Gln
20 25 30

Pro Gln Met Ala Leu Pro Thr Ala Asp Gly Pro Tyr Leu Gln Ile Leu
35 40 45

Glu Gln Pro Lys Gln Arg Gly Phe Arg Phe Arg Tyr Val Cys Glu Gly
50 55 60

Pro Ser His Gly Gly Leu Pro Gly Ala Ser Ser Glu Lys Asn Lys Lys
65 70 75 80

Ser Tyr Pro Gln Val Lys Ile Cys Asn Tyr Val Gly Pro Ala Lys Val
85 90 95

Ile Val Gln Leu Val Thr Asn Gly Lys Asn Ile His Leu His Ala His
100 105 110

Ser Leu Val Gly Lys His Cys Glu Asp Gly Ile Cys Thr Val Thr Ala
115 120 125

Gly Pro Lys Asp Met Val Val Gly Phe Ala Asn Leu Gly Ile Leu His
130 135 140

Val Thr Lys Lys Lys Val Phe Glu Thr Leu Glu Ala Arg Met Thr Glu
145 150 155 160

Ala Cys Ile Arg Gly Tyr Asn Pro Gly Leu Leu Val His Pro Asp Leu
165 170 175

Ala Tyr Leu Gln Ala Glu Gly Gly Gly Asp Arg Gln Leu Gly Asp Arg
180 185 190

Glu Lys Glu Leu Ile Arg Gln Ala Ala Leu Gln Gln Thr Lys Glu Met
195 200 205

Asp Leu Ser Val Val Arg Leu Met Phe Thr Ala Phe Leu Pro Asp Ser
210 215 220

Thr Gly Ser Phe Thr Arg Arg Leu Glu Pro Val Val Ser Asp Ala Ile
225 230 235 240

Tyr Asp Ser Lys Ala Pro Asn Ala Ser Asn Leu Lys Ile Val Arg Met
245 250 255

Asp Arg Thr Ala Gly Cys Val Thr Gly Gly Glu Glu Ile Tyr Leu Leu
260 265 270

Cys Asp Lys Val Gln Lys Asp Asp Ile Gln Ile Arg Phe Tyr Glu Glu
275 280 285

Glu Glu Asn Gly Gly Val Trp Glu Gly Phe Gly Asp Phe Ser Pro Thr
290 295 300

Asp Val His Arg Gln Phe Ala Ile Val Phe Lys Thr Pro Lys Tyr Lys
305 310 315 320

Asp Ile Asn Ile Thr Lys Pro Ala Ser Val Phe Val Gln Leu Arg Arg
325 330 335

Lys Ser Asp Leu Glu Thr Ser Glu Pro Lys Pro Phe Leu Tyr Tyr Pro
340 345 350

Glu Ile Lys Asp Lys Glu Glu Val Gln Arg Lys Arg Gln Lys Leu Met
355 360 365

Pro Asn Phe Ser Asp Ser Phe Gly Gly Gly Ser Gly Ala Gly Ala Gly
370 375 380

Gly Gly Gly Met Phe Gly Ser Gly Gly Gly Gly Gly Gly Thr Gly Ser
385 390 395 400

Thr Gly Pro Gly Tyr Ser Phe Pro His Tyr Gly Phe Pro Thr Tyr Gly
405 410 415

Gly Ile Thr Phe His Pro Gly Thr Thr Lys Ser Asn Ala Gly Met Lys
420 425 430

His Gly Thr Met Asp Thr Glu Ser Lys Lys Asp Pro Glu Gly Cys Asp
435 440 445

Lys Ser Asp Asp Lys Asn Thr Val Asn Leu Phe Gly Lys Val Ile Glu
450 455 460

Thr Thr Glu Gln Asp Gln Glu Pro Ser Glu Ala Thr Val Gly Asn Gly
465 470 475 480

Glu Val Thr Leu Thr Tyr Ala Thr Gly Thr Lys Glu Glu Ser Ala Gly
485 490 495

Val Gln Asp Asn Leu Phe Leu Glu Lys Ala Met Gln Leu Ala Lys Arg
500 505 510

His Ala Asn Ala Leu Phe Asp Tyr Ala Val Thr Gly Asp Val Lys Met
515 520 525

Leu Leu Ala Val Gln Arg His Leu Thr Ala Val Gln Asp Glu Asn Gly
530 535 540

Asp Ser Val Leu His Leu Ala Ile Ile His Leu His Ser Gln Leu Val
545 550 555 560

Arg Asp Leu Leu Glu Val Thr Ser Gly Leu Ile Ser Asp Asp Ile Ile
565 570 575

Asn Met Arg Asn Asp Leu Tyr Gln Thr Pro Leu His Leu Ala Val Ile
580 585 590

Thr Lys Gln Glu Asp Val Val Glu Asp Leu Leu Arg Ala Gly Ala Asp
595 600 605

Leu Ser Leu Leu Asp Arg Leu Gly Asn Ser Val Leu His Leu Ala Ala
610 615 620

Lys Glu Gly His Asp Lys Val Leu Ser Ile Leu Leu Lys His Lys Lys
625 630 635 640

Ala Ala Leu Leu Leu Asp His Pro Asn Gly Asp Gly Leu Asn Ala Ile
645 650 655

His Leu Ala Met Met Ser Asn Ser Leu Pro Cys Leu Leu Leu Leu Val
660 665 670

Ala Ala Gly Ala Asp Val Asn Ala Gln Glu Gln Lys Ser Gly Arg Thr
675 680 685

Ala Leu His Leu Ala Val Glu His Asp Asn Ile Ser Leu Ala Gly Cys

-continued 690 695 700

Leu Leu Leu Glu Gly Asp Ala His Val Asp Ser Thr Thr Tyr Asp Gly
705 710 715 720

Thr Thr Pro Leu His Ile Ala Ala Gly Arg Gly Ser Thr Arg Leu Ala
725 730 735

Ala Leu Leu Lys Ala Ala Gly Ala Asp Pro Leu Val Glu Asn Phe Glu
740 745 750

Pro Leu Tyr Asp Leu Asp Asp Ser Trp Glu Asn Ala Gly Glu Asp Glu
755 760 765

Gly Val Val Pro Gly Thr Thr Pro Leu Asp Met Ala Thr Ser Trp Gln
770 775 780

Val Phe Asp Ile Leu Asn Gly Lys Pro Tyr Glu Pro Glu Phe Thr Ser
785 790 795 800

Asp Asp Leu Leu Ala Gln Gly Asp Met Lys Gln Leu Ala Glu Asp Val
805 810 815

Lys Leu Gln Leu Tyr Lys Leu Leu Glu Ile Pro Asp Pro Asp Lys Asn
820 825 830

Trp Ala Thr Leu Ala Gln Lys Leu Gly Leu Gly Ile Leu Asn Asn Ala
835 840 845

Phe Arg Leu Ser Pro Ala Pro Ser Lys Thr Leu Met Asp Asn Tyr Glu
850 855 860

Val Ser Gly Gly Thr Val Arg Glu Leu Val Glu Ala Leu Arg Gln Met
865 870 875 880

Gly Tyr Thr Glu Ala Ile Glu Val Ile Gln Ala Ala Ser Ser Pro Val
885 890 895

Lys Thr Thr Ser Gln Ala His Ser Leu Pro Leu Ser Pro Ala Ser Thr
900 905 910

Arg Gln Gln Ile Asp Glu Leu Arg Asp Ser Asp Ser Val Cys Asp Thr
915 920 925

Gly Val Glu Thr Ser Phe Arg Lys Leu Ser Phe Thr Glu Ser Leu Thr
930 935 940

Ser Gly Ala Ser Leu Leu Thr Leu Asn Lys Met Pro His Asp Tyr Gly
945 950 955 960

Gln Glu Gly Pro Leu Glu Gly Lys Ile
965

What is claimed as new and desired to be secured by Letters Patent of the United States is:

1. A biologically pure protein, wherein said protein consists of the sequence shown in SEQ ID NO:1.

2. A biologically pure protein, wherein said protein consists of the sequence shown in SEQ ID NO:2.

* * * * *